United States Patent [19]

Morrison

[11] 4,309,085
[45] Jan. 5, 1982

[54] METHOD FOR MEASURING EYE FEATURES WITH A CONTACT LENS

[76] Inventor: Robert J. Morrison, Green and Division Sts., Harrisburg, Pa. 17110

[21] Appl. No.: 57,040

[22] Filed: Jul. 12, 1979

[51] Int. Cl.³ .......................... A61B 3/10; A61B 5/10; G02C 7/04
[52] U.S. Cl. .......................................... 351/39; 351/6; 351/160 H; D24/99
[58] Field of Search ........................... 351/160 R–162, 351/6, 39; D24/99; 128/745

[56] References Cited

U.S. PATENT DOCUMENTS 3,169,459  2/1965  Friedberg et al. ............... 351/160
4,194,814  3/1980  Fischer et al. .................. 351/160 R

FOREIGN PATENT DOCUMENTS 1552106  11/1968  France .......................... 351/160 R

*Primary Examiner*—John K. Corbin
*Assistant Examiner*—Scott J. Sugarman
*Attorney, Agent, or Firm*—Robert A. Green

[57] ABSTRACT

The disclosure is of a contact lens for use on the eye, the lens carrying indicia usable for measuring changes in the shape, size or length, or the like, of portions of the eye.

3 Claims, 4 Drawing Figures

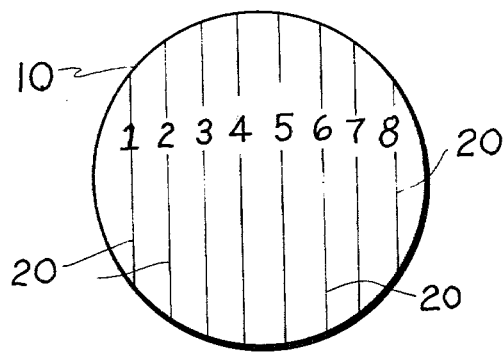
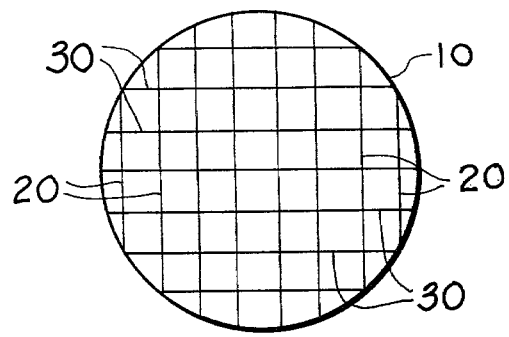
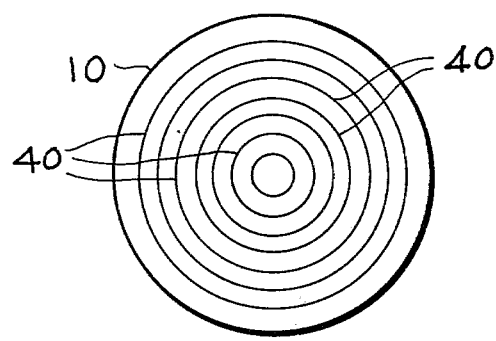
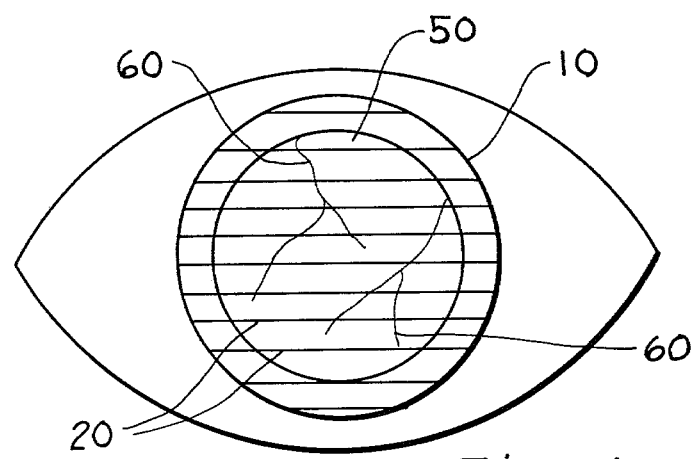

METHOD FOR MEASURING EYE FEATURES WITH A CONTACT LENS

BACKGROUND OF THE INVENTION

At present, there are problems or diseases of the eye in which the progress of the problem is monitored by measuring, from time to time, the size or shape of a visible feature in the eye. An example is the problem of neo-vascularization in which new blood vessels are generated. Other measurements medical personnel might make are of scar tissue, the diameter or cord of a normal cornea, lesions and cysts in various locations, and the like. At the present time, measuring operations of this type are carried out crudely, for the most part, by means of a rigid ruler or the like placed adjacent to the eye. It is clear that such methods of measuring are highly inaccurate and unsatisfactory in medical practice.

The present invention solves the problem described above by providing a contact lens which can be placed directly on the eye, the lens carrying markings or indicia usable for measuring visible features in the eye.

DESCRIPTION OF THE DRAWINGS

FIG. 1 is a front elevational view of one embodiment of the invention;

FIG. 2 is a front elevational view of another embodiment of the invention;

FIG. 3 is a front elevational view of still another embodiment of the invention; and FIG. 4 is a front elevational view of an eye and a contact lens embodying the invention in operative relation therewith.

DESCRIPTION OF THE PREFERRED EMBODIMENTS

Optical apparatus embodying the invention comprises a contact lens 10 which is adapted to be placed on the eye in well known fashion. The lens may be a so-called hard lens; however, it is preferably a soft lens, which provides more intimate contact with the eye. According to the invention, the lens carries markings or indicia of any suitable type, for example, a series of parallel lines 20 which may be oriented at any desired angle by suitable placement of the lens on the eye. The indicia might also be both horizontal and vertical lines 20 and 30 which form a grid, or they may be other straight line configurations. In addition, the indicia might be a series of concentric circles 40 spaced apart by equal amounts or by varying amounts, as desired. Other suitable indicia will occur to those skilled in the art. The indicia may carry numerical markings, if desired, as illustrated in FIG. 1.

The indicia described above may be formed in any suitable manner. For example, they might be formed on the outer surface of the lens by an ink marking operation after the lens has been formed, or they might be formed integrally with the lens when the lens is formed. The indicia might be formed by etching, engraving, or printing, and they might be formed by hand or by mechanical means.

In using the invention, referring to FIG. 4, the lens 10 having the desired indicia is placed on the eye 50, suitably oriented with respect to structural features to be measured, for example, blood vessels 60. The length or size of the vessels can be determined by reference to the indicia, and, if the measurement is performed from time to time, any change in the vessels can be detected. Again, it is to be noted that cysts, lesions, scars, and other features in the eye can be measured.

What is claimed is:

1. The method of measuring features of the eye comprising
   forming a soft contact lens having measuring indicia thereon,
   repeatedly placing said soft contact lens on the eye and in intimate engagement therewith, said lens overlying a changeable feature of the eye to be measured, and
   measuring said feature by means of said indicia each time the soft contact lens is placed on the eye.

2. The method of measuring phenonema in the eye comprising the steps of
   forming a soft contact lens having measuring indicia thereon,
   at a predetermined time, placing said lens on the eye overlying a feature of the eye to be measured whereby said feature occupies a portion of said measuring indicia, said lens intimately engaging the surface of the eye over its entire area,
   measuring said feature by means of said indicia,
   removing said contact lens from the eye, and
   at a later time, again placing said contact lens on the eye and measuring said feature and comparing the relationship of said feature to said measuring indicia, whereby the operator can determine the medical status of the feature and its change in dimensions with time.

3. The method defined in claim 2 and repeating the steps of inserting the contact lens and measuring the feature in the eye at spaced time intervals to follow the medical condition of said feature in the eye.

* * * * *